(12) United States Patent
Perlitz (10) Patent No.: US 6,394,955 B1
(45) Date of Patent: May 28, 2002

(54) DEVICE ATTACHABLE TO A THERAPEUTIC HEAD FOR ADJUSTABLY HOLDING AN ULTRASOUND TRANSDUCER, AND THERAPEUTIC HEAD IN COMBINATION WITH SUCH A DEVICE

(75) Inventor: Lucas Perlitz, Jena (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/495,857

(22) Filed: Feb. 1, 2000

(30) Foreign Application Priority Data

Feb. 1, 1999 (DE) .......................................... 199 03 877
Oct. 29, 1999 (DE) ..................................... 299 19 084 U (51) Int. Cl.[7] .............................................. A61B 17/22
(52) U.S. Cl. .............................. 600/439; 601/2; 601/3; 601/4
(58) Field of Search .............................. 600/439, 459; 601/2, 3, 4; 606/127, 128

(56) References Cited

U.S. PATENT DOCUMENTS

| 4,669,483 A | | 6/1987 | Hopp et al. | |
| 4,932,414 A | * | 6/1990 | Coleman et al. | 128/916 |
| 5,003,965 A | * | 4/1991 | Talish et al. | |
| 5,054,470 A | * | 10/1991 | Fry et al. | |
| 5,095,908 A | * | 3/1992 | Belikan et al. | |
| 5,152,289 A | | 10/1992 | Viebach et al. | |
| 5,243,986 A | * | 9/1993 | Wurster | 600/439 |
| 5,315,986 A | * | 5/1994 | Lacruche et al. | |
| 5,762,616 A | * | 6/1998 | Talish | |
| 6,007,499 A | * | 12/1999 | Martin et al. | |
| 6,036,661 A | * | 3/2000 | Schwarze et al. | 600/439 |

FOREIGN PATENT DOCUMENTS

DE PS 40 03 350 4/1991

* cited by examiner

Primary Examiner—Brian L. Casler
(74) Attorney, Agent, or Firm—Schiff Hardin & Waite (57) ABSTRACT

A device for adjustably holding an ultrasonic transducer having an acoustic axis can be attached at a therapeutic head which emits acoustic waves converging in a focus. The device has at least one element which can be swivelled around a first swivel axis of the device. The ultrasonic transducer is at least indirectly attachable at the element such that its acoustic axis proceeds substantially through the focus of the therapeutic head and the swivel axis proceed substantially through the focus of the therapeutic head when the device is attached at the therapeutic head.

32 Claims, 6 Drawing Sheets

DEVICE ATTACHABLE TO A THERAPEUTIC HEAD FOR ADJUSTABLY HOLDING AN ULTRASOUND TRANSDUCER, AND THERAPEUTIC HEAD IN COMBINATION WITH SUCH A DEVICE

BACKGROUND OF THE INVENTION

1. Field of the Invention

The present invention is directed to a device for accepting an ultrasonic transducer having an acoustic axis, the device being attachable to a therapeutic head that contains means for generating acoustic waves converging in a focus, the device allowing the ultrasonic transducer to be attached at the device such that its acoustic axis proceeds substantially through the focus of the therapeutic head. The invention is also directed to the combination of a therapeutic head and such a device.

2. Description of the Prior Art

German PS 39 15 384 discloses a device of the general type described above. The device has a ring, which is arranged at the therapeutic head and which can be rotated around the therapeutic head; the rotational axis of the ring coinciding with the acoustic axis of the therapeutic head. A lever arm with three levers that can be rotated around rotational axes is arranged at the ring, this lever arm guiding the ultrasonic transducer in a restricted manner such that the ultrasonic transducer is always aimed at the focus of the therapeutic head given rotations of the ring around its rotational axis and given slewing motions of the levers of the lever arm around their rotational axes.

The advantage of such an arrangement for guidance of an ultrasonic transducer relative to a therapeutic head is that, for example, the orientation of the focus of the therapeutic head of a lithotripter provided with such a device toward a calculus, which is to be disintegrated in the body of a living organism, is facilitated, since the acoustic axis of the ultrasonic transducer is always directed toward the focus of the therapeutic head independently of adjustment motions or scan motions of the ultrasonic transducer with the device for the purpose of locating the calculus within the body by ultrasound. In this way, the focus of the therapeutic head can be displaced in a simple way under ultrasonic control relative to the calculus to be disintegrated with focused acoustic waves, by means of adjusting the therapeutic head relative to the living organism.

German PS 34 27 001 describes a therapeutic device for the contact-free disintegration of calculi in the body of a patient, which has a shockwave focusing chamber arranged in a tub, in which a patient is seated, and which has a locating and positioning device, which is provided with an ultrasonic transducer and which can be adjusted relative to the focus of the shockwave focusing chamber. The locating and positioning device has a C-bend guide that can be positioned around the body of the patient. At this guide, the ultrasonic transducer can be displaced over a larger region of the body. For marking or registering the position or the position and the direction of the ultrasonic transducer with respect to the focus of the shockwave focusing chamber, corresponding devices are provided at the therapeutic device, for example, position sensors and/or angle transmitters.

Further, German OS 39 32 364 discloses a spherical-cap-shaped therapeutic transducer for use for disintegrating objects inside of the body. An ultrasonic transducer is integrated into the therapeutic transducer for locating the objects to be disintegrated, the ultrasonic transducer being adjusted in a confocal manner relative to the therapeutic transducer.

The technically complicated structures of these known devices represent a disadvantage.

SUMMARY OF THE INVENTION

An object of the present invention is to a device of the type described above having a structure that is technically simple and therefore inexpensive. A further object of the invention is to provide a therapeutic head such that the device can be variably arranged at the therapeutic head.

This object is inventively achieved in a device for movably holding an ultrasonic transducer having an acoustic axis, the device being attachable at a therapeutic head that contains means for generating acoustic waves converging in a focus, and having at least one element that can be swivelled around a swivel axis of the device, the ultrasonic transducer being mounted at the element such that its acoustic axis proceeds substantially through the focus of the therapeutic head when the device is attached at the therapeutic head, and wherein the swivel axis proceeds substantially through the focus of the therapeutic head when the device is attached at the therapeutic head. The inventive device has only one element at which the ultrasonic transducer is arranged and which can be swivelled around a swivel axis of the device. Therefore, the device is structured extremely simply and inexpensively. Preferably, the ultrasonic transducer is arranged at the element such that it can be displaced along its acoustic axis, so that it can be rested against the surface of a body of a living organism to be treated with acoustic waves. In this case, measuring elements that register displacements are preferably allocated to the ultrasonic transducer in order to enable an exact mixing of the position of the focus into the ultrasonic images acquired with the ultrasonic transducer given a displacement of the ultrasonic transducer. Because the swivel axis proceeds substantially through the focus of the therapeutic head given a device attached at the therapeutic head, the acoustic axis of the ultrasonic transducer also always proceeds substantially through the focus of the therapeutic head given swiveling of the element around the swivel axis. Therefore, the swivel of the element around the rotational axis enables positioning of the ultrasonic transducer, for example, when observing the disintegration process of a calculus in the body of a patient, at different locations of the body surface of the patient without losing the relation to the focus of the therapeutic head.

In a preferred embodiment of the invention the element is fashioned in a curved manner. According to a version of the invention, the bent element is substantially circularly curved, with the center of curvature of the bent element substantially coinciding with the focus of the therapeutic head given a device arranged at the therapeutic head.

In further versions of the invention provide that the ultrasonic transducer can be adjusted along the circumference of the bent element, or the ultrasonic transducer can be attached at a holding device, which is adjustable along the circumference of the bent element. Thus, the ultrasonic transducer can be adjusted in a practically spherical manner within a spherical segment by swivelling of the bent element around the swivel axis and by displacement of the ultrasonic transducer, or the holding device for the ultrasonic transducer along the circumference of the bent element. The device thus offers a number of possibilities for positioning the ultrasonic transducer with respect to the body surface of a patient to be examined and to be treated with acoustic waves.

In another embodiment of the invention, the bent element of the device has an opening in the form of a slot, this opening extending in the circumferential direction, and a holding device, for the ultrasonic transducer can be adjusted in the opening in the circumferential direction of the bent element. This structure of the device with a holding device for the ultrasonic transducer, with the holding device being adjustable in such an opening, effects a stabilization of the adjustment movement of the holding device and the ultrasonic transducer.

In a further version of the invention, the holding device is circularly curved at least in the area in which the ultrasonic transducer is arranged at the holding device, with the center of curvature of the holding device substantially coinciding with the focus of the therapeutic head when the device is attached at the therapeutic head. The ultrasonic transducer is preferably arranged adjustably in the holding device, or at the holding device. Thus, apart from the adjustment of the holding device of the ultrasonic transducer in the circumferential direction of the bent element, further adjustment possibilities are available for the ultrasonic transducer with respect to the body surface of a living organism to be treated with the therapeutic head, by adjusting the ultrasonic transducer in the circularly curved holding device, or at the circularly curved holding device. Inventively, the acoustic axis of the ultrasonic transducer is always directed substantially toward the focus as a result of the circular curvature of the bent element and the holding device.

In a further embodiment of the invention, a second bent element is provided, which is arranged essentially parallel to the first bent element, with the holding device connecting the two bent elements. A stabilization of the adjustment process of the holding device can also be effected in this way when the holding device is adjustable in the circumferential direction of the bent elements.

In another embodiment of the invention, at least one further element is provided, which element is connected to the first element preferably via a pivot having a swivel axis and which, relative to the first element, can be swivelled around this swivel axis of the pivot. Preferably, the first element and the further element are each fashioned in a bent, circularly curved manner. This embodiment of the invention makes it possible, for example, to turn the one element such that it rests substantially at the first bent element. Given the orientation of the focus of the therapeutic head toward a calculus to be disintegrated or toward a body tissue to be treated, the second bent element is preferably folded out and forms a bend with the first bent element, at which bend the ultrasonic transducer is adjustably arranged, for example, in the circumferential direction. During the examination process or therapy process, the second bent element can be turned around the rotational axis, so that a compact arrangement of the bent elements is achieved.

In a preferred embodiment of the invention, the first element and the second element can have a common swivel axis, which forms a second swivel axis of the device. The two elements can be adjusted relative to one another around this common swivel axis, which proceeds substantially through the focus of the therapeutic head given a device arranged at the therapeutic head. Preferably, the first element and the second element are each fashioned in a bent manner. For example, when the ultrasonic transducer can be arranged at the second bent element and the first bent element of the device can be additionally swivelled around the initially described swivel axis of the aforementioned device, making possible a spherical movement of the ultrasonic transducer within a spherical segment and thereby allowing variable positioning of the ultrasonic transducer relative to the body surface of a living organism to be treated.

In a further version of the invention a number of elements, which are preferably fashioned in a bent manner, and which are movable relative to one another, form a chain at which the ultrasonic transducer is arranged. These elements alternatively can be arranged in the form of a telescopic arm with the ultrasonic transducer fastened at one end. In another version of the invention the device has two spherically curved plates, which are arranged at the therapeutic head and whose centers of curvature substantially coincide with the focus of the therapeutic head given a device arranged at the therapeutic head. The plates contain an intermediate space therebetween with a substantially constant gap width in which the bent element is adjustably held. In this version, the ultrasonic transducer also can be moved relative to the therapeutic head in a technically simple way such that its acoustic axis always proceeds substantially extends through the focus of the therapeutic head.

The above object is also achieved in a therapeutic head which has at least two fastening arrangements that are appropriate for variably attaching a holder device as described above. Thus, the holder device can be fastened at at least two different locations of the therapeutic head, so that the ultrasonic transducer can be positioned relative to the body surface of a patient in multiple ways.

DESCRIPTION OF THE PREFERRED EMBODIMENTS

Figure 1:
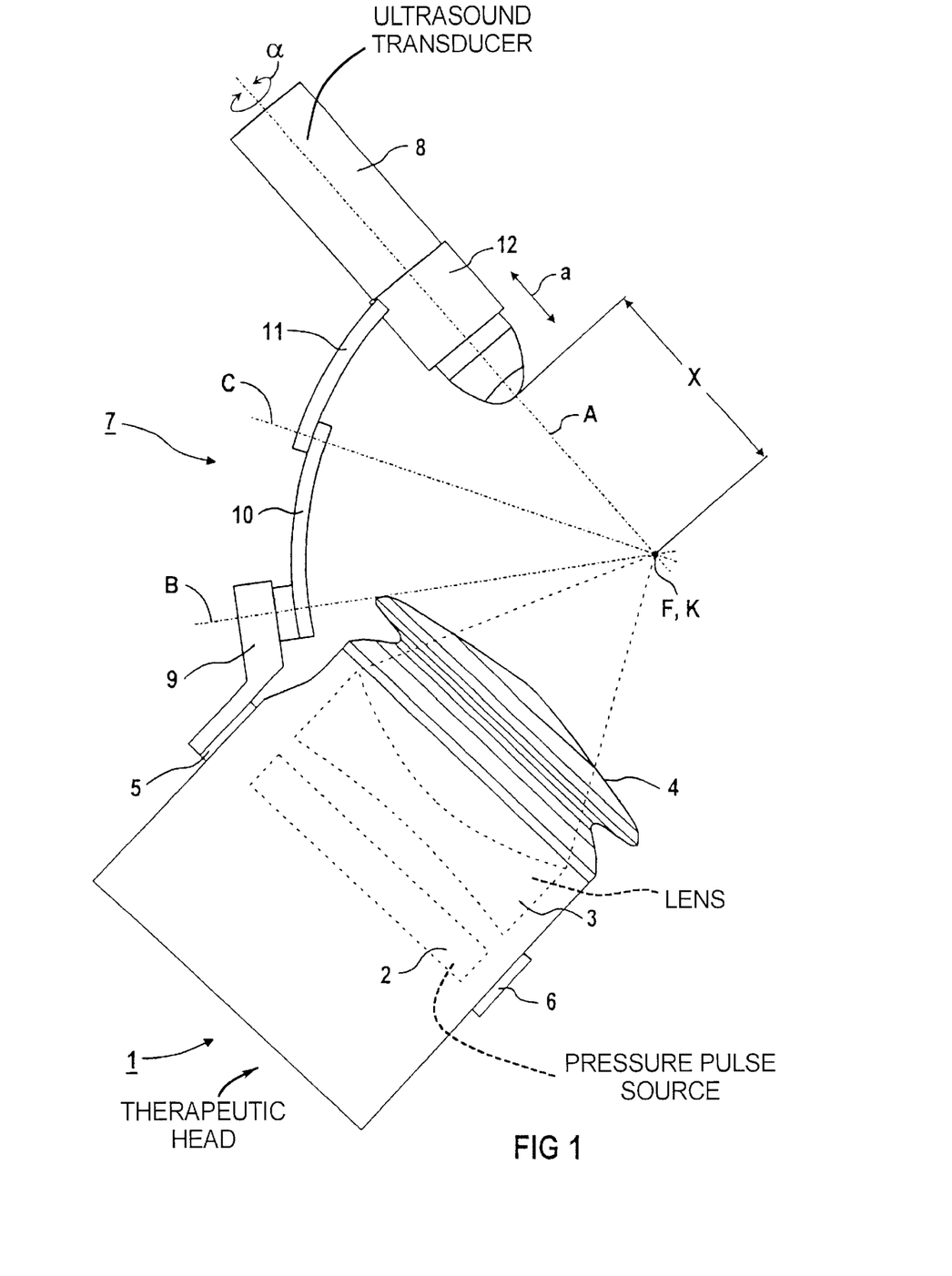
FIG. 1 shows an inventive device arranged at a therapeutic head for accepting and guiding an ultrasonic transducer with two bent, circularly curved elements.

FIG. 1 shows a therapeutic head 1 of an apparatus (not fully shown in FIG. 1) for the treatment of body tissue, in particular for disintegrating calculi or treating tissue in the body of a living organism with focused acoustic waves. The therapeutic head 1 has known means (only schematically shown) for generating focused acoustic waves. A pressure pulse source 2 and a convex lens 3 are shown in FIG. 1 as examples for such means. In the exemplary embodiment, the acoustic waves that proceed from the pressure pulse source 2 are focused on the focus F, which is a three-dimensional focus zone in practice, by means of the convex lens 3. At the patient side, the therapeutic head 1 is provided with a flexible coupling cushion 4, which is filled with an acoustic propagation medium, for the coupling and introduction of the acoustic waves generated by the pressure pulse source 2 into the body of a patient (not shown in FIG. 1). In a known way, the therapeutic head 1 can be adjusted relative to the patient in order to be able to displace the focus F of the therapeutic head 1 to coincide with the tissue to be treated, or the calculus to be disintegrated. The patient or a patient table supporting the patient also or alternatively can be adjusted relative to the therapeutic head 1 for displacement of the focus F of the therapeutic head 1 to the tissue to be treated, or to the calculus to be disintegrated.

In the exemplary embodiment, two attachment sites 5, 6 are arranged at the therapeutic head 1. A device 7 for accepting and guiding an ultrasonic transducer having an acoustic axis A can be fastened at either of the attachment sites 5, 6 by fasteners, for example, screws or clips. The attachment sites 5, 6 have guiding means or centering means (not explicitly shown), so that the device 7 can be arranged at the therapeutic head 1 in a defined and reproducible way.

The device 7 shown in FIG. 1 has a pivot 9 fastened at the attachment site device 5. A first bent, in this case circularly curved, element 10 is arranged at the pivot 9 in exemplary embodiment. The center of curvature K of the element 10 substantially coincides with the focus F of the therapeutic head 1. Therefore, the center of curvature K is the center of the circle, which center extends through the circularly curved element 10 and which has the same curvature as the element 10. The bent element 10 can be swivelled around a swivel axis B that extends through the pivot 9 and the element 10. A second bent, in this case also circularly curved, element 11, which has the same center of curvature K as the first bent element 10, is arranged at the first bent element 10. The element 11, relative to the element 10, can be swivelled around a swivel axis C that extends through the element 10 and the element 11. The swivel axes B and C respectively proceed substantially through the focus F of the therapeutic head 1 given a device 7 arranged at the therapeutic head 1.

A holding device 12 for accepting an ultrasonic transducer 8 is fastened at the element 11. The ultrasonic transducer 8 is accepted in the holding device 12 such that the acoustic axis A of the ultrasonic transducer 8 proceeds substantially through the focus F of the therapeutic head 1. The ultrasonic transducer 8 is accepted in the holding device 12 such that it can be adjusted in the direction of its acoustic axis A (indicated by the double arrow a) and such that it can be rotated around its acoustic axis A (indicated by the double arrow α).

The device 7, which guides the ultrasonic transducer 8 in a restricted manner such that its acoustic axis A always proceeds substantially through the focus F of the therapeutic head 1, facilitates the orientation of the focus F toward, for example, a treatment area (not shown in FIG. 1) that lies in the body of a patient. The position of the focus F is known in the ultrasonic images acquired with the ultrasonic transducer 8, or the position of the focus F can be easily determined by a distance marker representing the distance x entered in FIG. 1 which can be mixed into the ultrasonic images. The determination of the distance x can ensue in a known manner, for example, in the course of a calibration using a focus phantom. Additionally, the holding device 7 is preferably provided with measuring means, for example, scales or electrically operated position sensors, for example, a linear potentiometer, in order to determine the position of the ultrasonic transducer 8 relative to the focus F of the therapeutic head 1, or in order to determine the distance x of the ultrasonic transducer 8 from the focus F and in order to be able to correspondingly mix the position of the focus F into the ultrasonic images given displacements of the ultrasonic transducer 8 in the direction of its acoustic axis A. The device 7 allows spherical movement of the ultrasonic transducer 8 within a spherical segment around the rotational axes B, C due to the rotation of the elements 10, 11, so that the ultrasonic transducer 8 can be placed in a position, relative to a patient to be treated, which is beneficial for the acquisition of ultrasonic images.

Should the attachment of the device 7 at the attachment site 5 prove to be inappropriate for acquiring ultrasonic images, the device 7 can be arranged alternatively at the attachment site 6. Apart from the attachment sites 5 and 6, further attachment sites can be provided at the therapeutic head 1 for defined and reproducible fastening of the device 7. The attachment sites are respectively located such that the acoustic axis A of the ultrasonic transducer 8 always proceeds substantially through the focus F of the therapeutic head 1 given the arrangement of the device 7 at one of the attachment sites.

Further exemplary embodiments of the invention are shown in the following figures, wherein elements of the devices, which are at least essentially the same regarding construction and function, are provided with the same reference numbers.

Figure 2:
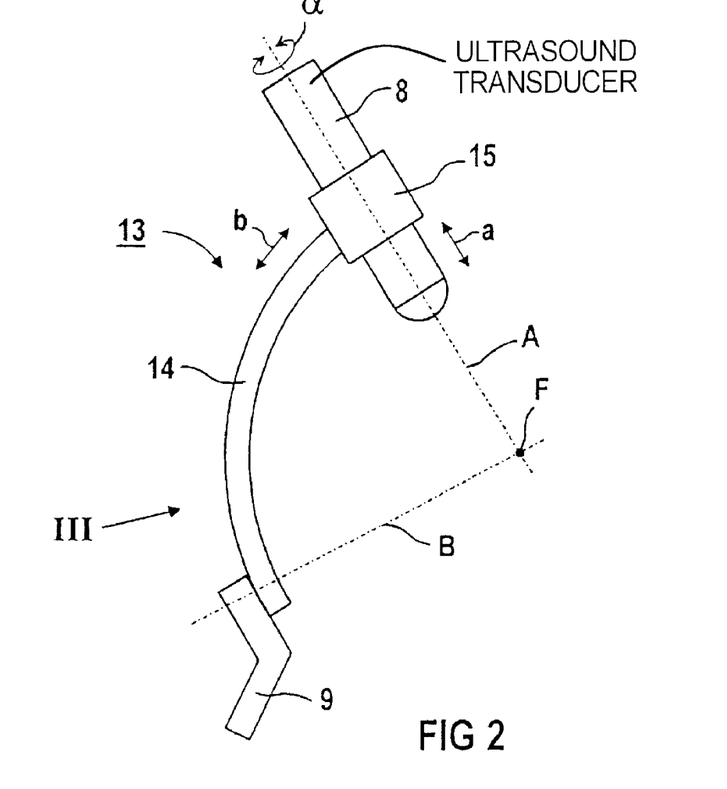
FIG. 2 shows an inventive device that can be attached at a therapeutic head with a bent, circularly curved element and with an adjustable holding device for the ultrasonic transducer.

FIG. 2 shows a different embodiment of a device 13 for accepting and guiding the ultrasonic transducer 8. The device 13 has only one bent element 14, which also is circularly curved and which has a center of curvature that coincides with the focus F of the therapeutic head (not shown) given attachment of the device 13 at the therapeutic head 1 (of FIG. 1). The element 14 is mounted at a pivot 9 for swivelling around the swivel axis B. As already described in the context of FIG. 1, the pivot 9 can be arranged at one of the attachment sites 5, 6 of the therapeutic head 1. The ultrasonic transducer 8 is accepted in a holding device 15, which can be adjusted along the circumference of the element 14. The ultrasonic transducer 8, in turn, is accepted in the holding device 15 such that it can be displaced along its acoustic axis A and such that it can be rotated around its acoustic axis A (double arrows a and α). Due to the swivelling of the element 14 around the swivel axis B and due to the displacement of the holding device 15 along the circumference of the element 14, the ultrasonic transducer 8, in turn, can be spherically adjusted within a spherical segment and thereby can assume different positions relative to a patient to be treated with the therapeutic head 1, for locating tissue to be treated or calculi to be disintegrated and for orientation of the therapeutic head 1.

Figure 3:
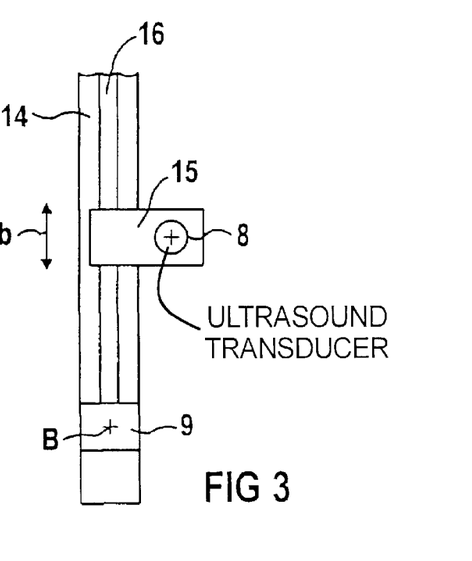
FIG. 3 schematically shows the inventive device of FIG. 2 in the direction of the arrow III as seen in FIG. 2.

FIG. 3 schematically shows a view in the direction of the arrow III from FIG. 2, whereby the holding device 15 is adjusted in the direction of the pivot 9. In the exemplary embodiment, the holding device 15 adjustably slides along a raised rail (or alternatively, a channel) that is arranged along the inner circumference of the element 14 and which the holding device engages. However, the holding device can also be adjustably arranged at the element 14 in a different way.

Figure 4:
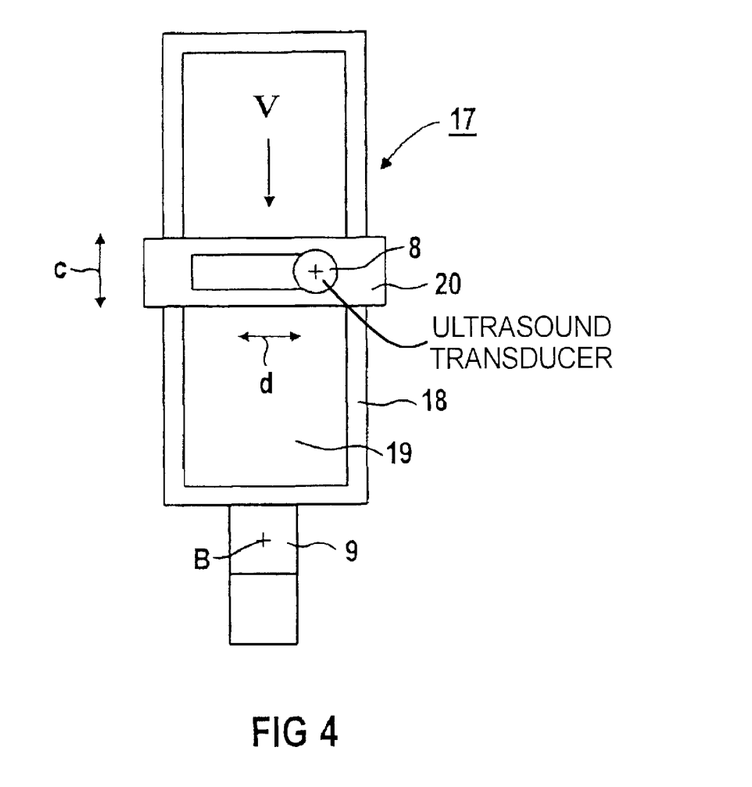
FIG. 4 shows an inventive device that can be attached at a therapeutic head with a bent, circularly curved element having an opening and a holding device that can be adjusted in the opening.
Figure 5:
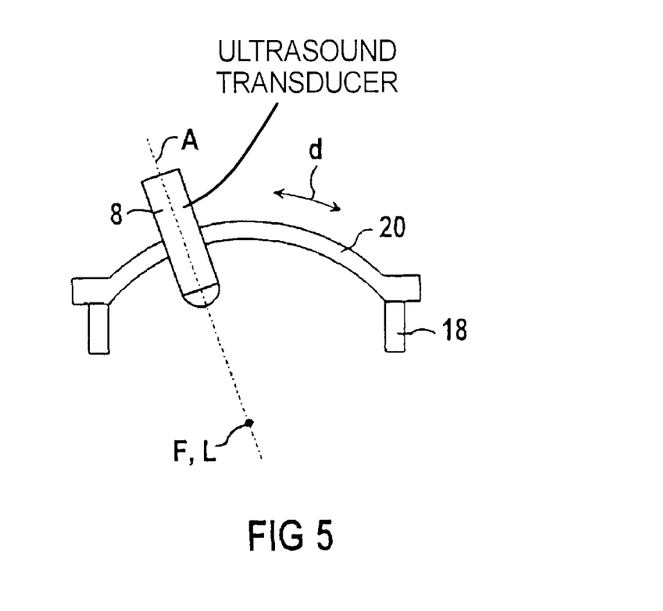
FIG. 5 schematically shown the inventive device of FIG. 4 in the direction of the arrow V as seen in FIG. 4.

FIG. 4, which corresponds to the view of FIG. 3 with respect to the direction of the view, shows a device 17 with a bent, again a circularly curved, element 18 whose center of curvature substantially coincides with the focus F of the therapeutic head given a device 17 attached at the therapeutic head 1. The element 18 has an opening 19 in the form of a slot, the opening 19 extending in the circumferential direction and along which a holding device 20 for the acceptance and guidance of the ultrasonic transducer 8 can be adjusted (double arrow c). FIG. 5 schematically shows the holding device 20 as seen in the direction of the arrow V from FIG. 4. In the area that is provided for the acceptance of the ultrasonic transducer 8, the holding device 20 is fashioned in a circularly curved manner, whereby the center of curvature L of the holding device 20 substantially coincides with the focus F of the therapeutic head given a device 17 attached at the therapeutic head. The ultrasonic transducer 8 is adjustable in the holding device 20 in the directions of the double arrow d, for example, in an angle range of ±11° proceeding from a middle position, the adjustment of the ultrasonic transducer 8 always ensuing such that its acoustic axis, along which the ultrasonic transducer 8 is adjustable and around which the ultrasonic transducer 8 is rotatable, proceeds substantially through the focus F of the therapeutic head 1. The element 18 is arranged at the pivot 9 and thus can be swivelled around the swivel axis B. Thus, the device 17 also offers the possibility to spherically adjust the ultrasonic transducer 8 within a spherical segment, for example, relative to the body surface of a patient to be treated with the therapeutic head 1.

Figure 6:
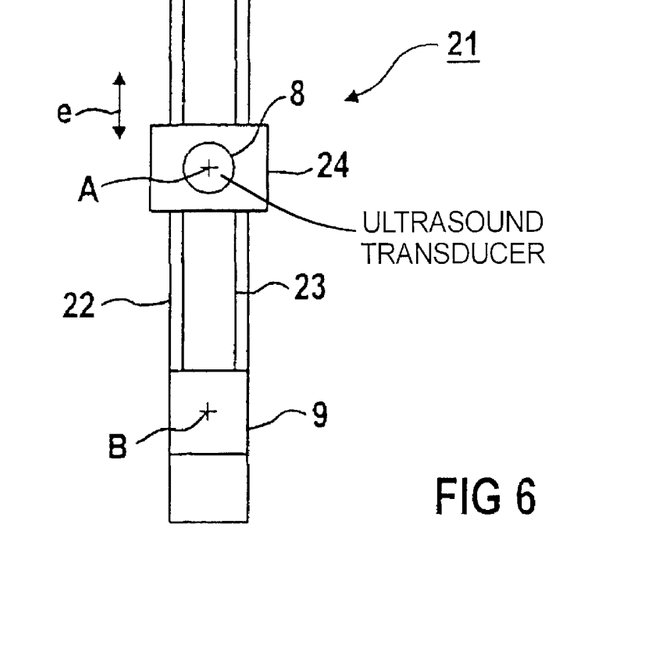
FIG. 6 schematically illustrates an inventive device with two bent, circularly curved elements that are arranged parallel to one another.

FIG. 6 shows a further embodiment in a view comparable to the view shown in FIG. 4 a device 21. This embodiment has the pivot 9 that can be attached at one of the attachment sites 5, 6 of the therapeutic head 1, two bent, again circularly curved, elements 22, 23 that are fastened at the pivot 9 and that are substantially parallel to one another, and a holding device 24, which engages the elements 22, 23, for the acceptance and guidance of the ultrasonic transducer 8. The centers of curvature of the elements 22, 23 substantially coincide with the focus F of the therapeutic head 1 given a device 21 arranged at the therapeutic head 1. The elements 22, 23 can be swivelled around the swivel axis B of the pivot 9. The holding device 24 is adjustable in the directions of the double arrow e along the circularly curved elements 22, 23. In the previously described way, the ultrasonic transducer 8 can be accepted in the holding device 24 such that it can be displaced along its acoustic axis A and such that it can be rotated around its acoustic axis A, with the acoustic axis A of the ultrasonic transducer 8 proceeding substantially through the focus F of the therapeutic head 1 given the device 21 attached at the therapeutic head 1. Due to the swivelling of the bent elements 22, 23 around the axis B of the pivot 9 and due to the displacement of the holding device 24 in the circumferential direction along the elements 22, 23, the ultrasonic transducer 8, in turn, can be spherically adjusted within a spherical segment, for example, relative to the body surface of a patient to be treated.

Figure 7:
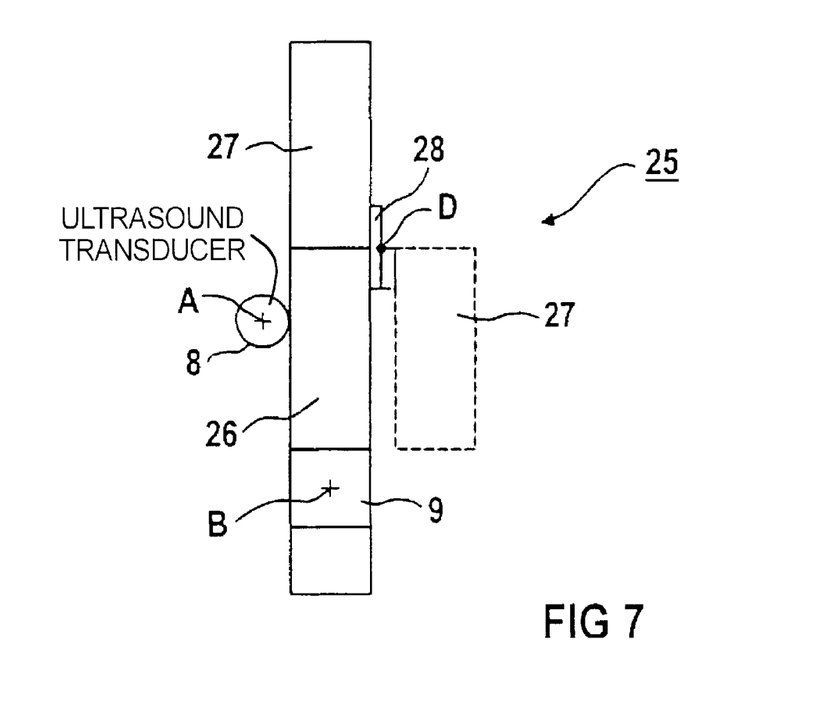
FIG. 7 schematically illustrates an inventive device with two bent, circularly curved elements, one of which can be turned around a rotational axis.

FIG. 7 shows a device 25 in a view comparable to the view shown in FIG. 4. The device 25 has the pivot 9 that can be attached at one of the attachment sites 5, 6 of the therapeutic head 1, and a first bent, again circularly curved, element 26 is arranged at the pivot 9. Additionally, the device 25 has a second bent, circularly curved element 27, which is connected to the first element 26 via a pivot 28. The centers of curvature of the elements 26,27 substantially coincide with the focus F when the device 25 is arranged at the therapeutic head 1 and the swivel axis D of the pivot 28 proceeds substantially through the focus F of the therapeutic head 1 of the exemplary embodiment, but the swivel axis D need not necessarily proceed through the focus F of the therapeutic head. The pivot 28 makes it possible to turn the element 27 with respect to the element 25 as shown in broken lines in FIG. 7. Thus, a longer bent, circularly curved element that comprises the elements 26, 27 can be produced as needed or a shorter bent, circularly curved element can be realized by turning the element 27 around the axis D of the pivot 28, if the total length proves to be disturbing or proves to be not expedient. The ultrasonic transducer 8 is mounted so as to be adjustable along the circumference of the elements 26, 27, so that its acoustic axis A is always directed toward the focus F of the therapeutic head 1 when the device 25 is attached at the therapeutic head 1.

Figure 8:
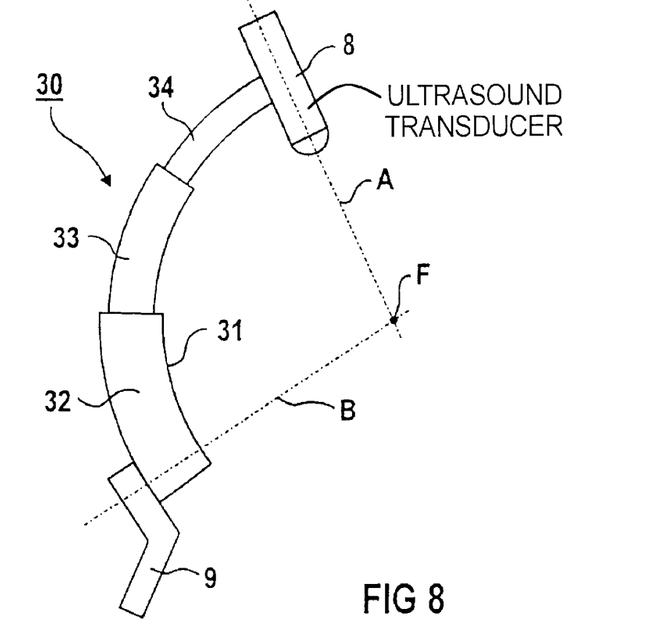
FIG. 8 shows an inventive device that can be attached at a therapeutic head in the form of a telescopic arm.

FIG. 8 shows a further embodiment of an inventive device 20 for the acceptance and guidance of the ultrasonic transducer 8. The device 20 has the pivot 9 that can be attached at one of the attachment sites 5, 6 of the therapeutic head 1 and a telescopic arm 31 that is fastened at the pivot 9 and that can be swivelled around the swivel axis B of the pivot 9. In the exemplary embodiment, the telescopic arm 31 has three bent, in this case circularly curved, elements 32 through 34. The centers of curvature of the elements 32 through 34 substantially coincide with the focus F of the therapeutic head when the device 30 is arranged at the therapeutic head 1. The elements 33, 34 are telescopically withdrawable. The ultrasonic transducer 9 is arranged at the free end of the element 34 such that the acoustic axis A of the ultrasonic transducer 8 proceeds substantially through the focus F of the therapeutic head 1 when the telescopic arm 31 is attached at the therapeutic head 1. The ultrasonic transducer 8 does not have to be immediately arranged at the free end of the element 34 as shown in FIG. 8; rather, a holding device in the form of the holding device 20 shown in FIG. 5 can be provided for accepting the ultrasonic transducer 8. Given arrangement of the device 30 at the therapeutic head 1, the device 30 enables spherical adjustment of the ultrasonic transducer 8 within a spherical segment relative to the body surface of a patient to be treated with the therapeutic head 1 by the swivelling of the telescopic arm 31 around the swivel axis B and by adjusting the elements 32 through 34 relative to one another.

Figure 9:
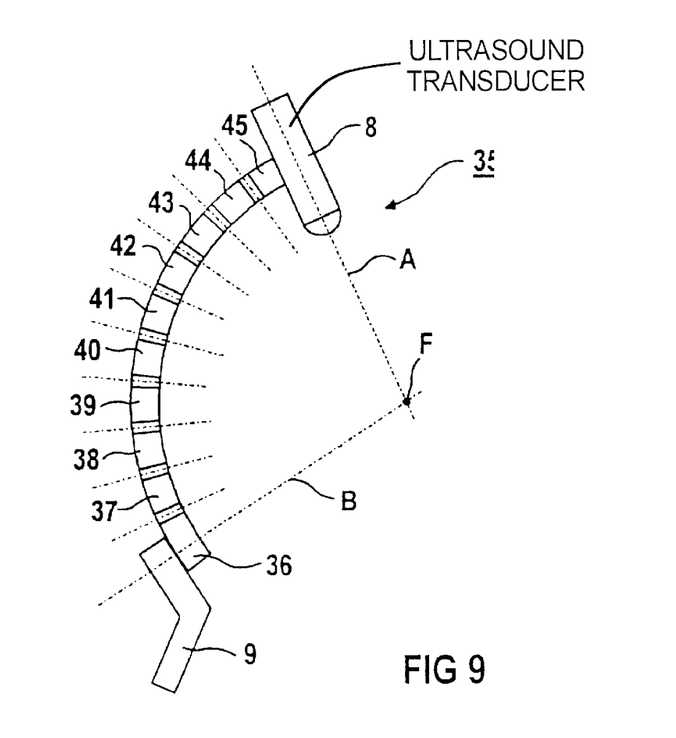
FIG. 9 shows an inventive device that can be attached at a therapeutic head with a number of bent, circularly curved elements that can be moved relative to one another.

FIG. 9 shows an embodiment of a device 35 for the acceptance and guidance of an ultrasonic transducer 8 with the pivot 9 that can be attached at one of the attachment sites 5, 6 of the therapeutic head 1 and with a number of bent, in this case circularly curved, elements 36 through 45 whose centers of curvature substantially coincide with the focus F of the therapeutic head 1 when the device 35 is arranged at the therapeutic head 1. The elements 36 through 45 form a chain and they can be rotated around axes relative to one another (schematically indicated in FIG. 9), these axes proceeding substantially through the focus F of the therapeutic head 1 when the device 35 attached at the therapeutic head 1. In the exemplary embodiment, the ultrasonic transducer 8 can be arranged at the free end of the element 45 such that the acoustic axis A of the ultrasonic transducer 8 proceeds substantially through the focus F of the therapeutic head 1. The ultrasonic transducer 8 alternatively can be arranged in a holding device arranged at the element 45, for example, in a holding device in the form of the holding device 20 from FIG. 5. Given arrangement of the device 35 at the therapeutic head 1, the device 35 enables spherical adjustment of the ultrasonic transducer 8 within a spherical segment relative to the body surface of a patient to be treated by the swivelling of the chain around the axis B of the pivot 9 and by adjusting the elements 36 through 45 relative to one another.

Figure 10:
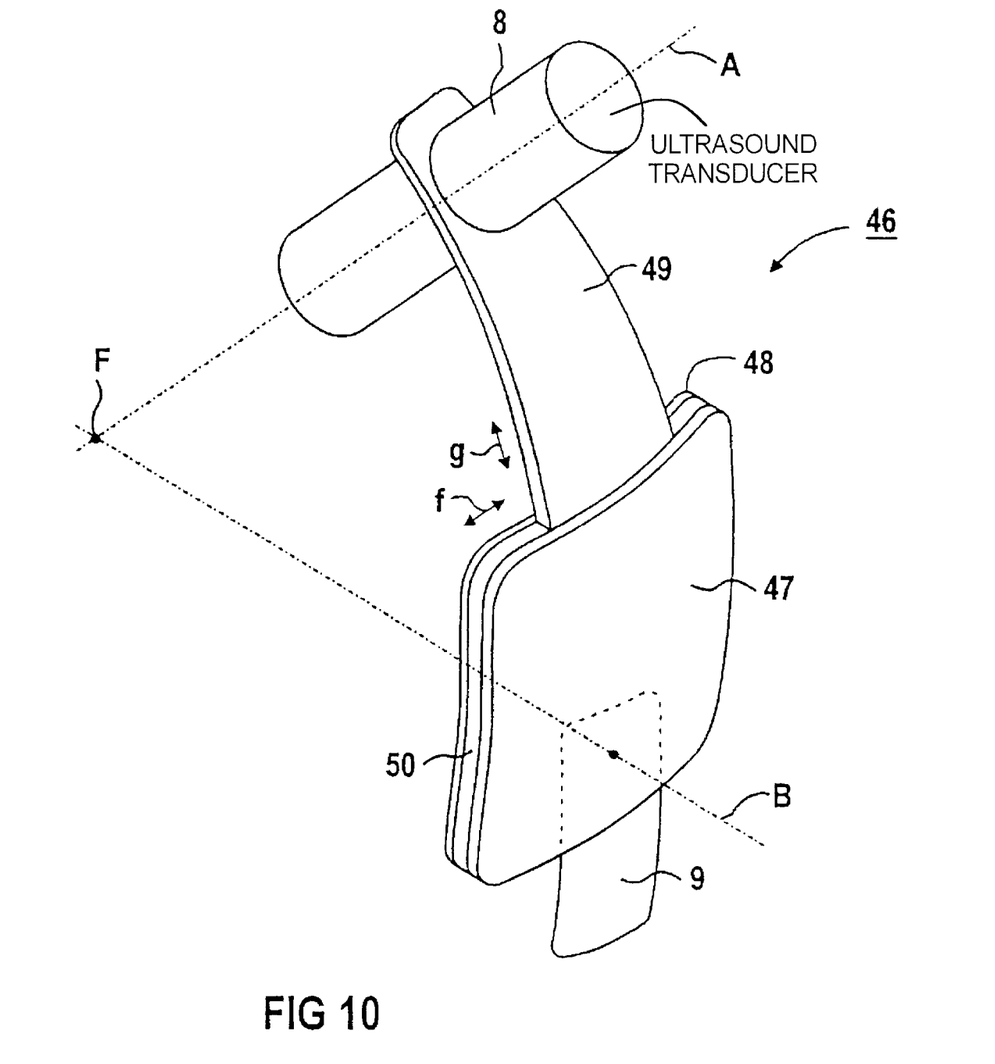
FIG. 10 shows an inventive device that can be attached at a therapeutic head with two spherically curved plates between which a bent, circularly curved element is adjustably arranged.

FIG. 10 shows a device 46 for the acceptance and guidance of the ultrasonic transducer 8, the device 46 having the pivot 9 that can be attached at one of the attachment sites 5, 6 of the therapeutic head 1, two spherically curved plates 47, 48 whose centers of curvature substantially coincide with the focus F of the therapeutic head 1 when the device 46 is arranged at the therapeutic head 1, and a bent, in this case circularly curved, element 49 whose center of curvature also substantially coincides with the focus F of the therapeutic head 1 when the device 46 is arranged at the therapeutic head 1. The plates 47, 48, which are fastened at the pivot 9, are arranged relative to one another such that they contain an intermediate space 50 therebetween with a substantially constant gap. In the intermediate space 50, the bent element 49 is adjustably supported in the directions of the double arrows f and g. The ultrasonic transducer 8 is arranged at the curved element 49 such that its acoustic axis A proceeds substantially through the focus F of the therapeutic head 1 when the device 46 is attached at the therapeutic head 1. Given arrangement of the pivot 9 at one of the attachment sites 5, 6 of the therapeutic head 1, the device 46 also makes it possible to spherically move the ultrasonic transducer 8 within a spherical segment around the focus F of the therapeutic head 1. Thus, the ultrasonic transducer 8 can be moved in a simple way, for example, over the body surface of a patient to be treated with the therapeutic head 1 for the acquisition of ultrasonic images from the inside of the body of the patient, with the relation of the acoustic axis A of the ultrasonic transducer 8 to the focus F of the therapeutic head 1 always being maintained.

The above described embodiments of the inventive device are to be understood only exemplary. In particular, mixtures of the above described embodiment can be devised.

Further, the elements of the devices are fashioned in a bent manner in the above described exemplary embodiments, however, this need not necessarily be the case. Rather, the elements can have a different shape, for example, they can be linear as long as the acoustic axis A of the ultrasonic transducer held by a device proceeds substantially extends through the focus of the therapeutic head when the device is attached at the therapeutic head 1.

Although modifications and changes may be suggested by those skilled in the art, it is the intention of the inventor to embody within the patent warranted hereon all changes and modifications as reasonably and properly come within the scope of his contribution to the art.

I claim as my invention:

1. An adjustable device comprising:
   a first part adapted for attachment to a therapeutic head which emits acoustic waves converging at a focus; and
   a second part adapted for holding an ultrasound transducer having an acoustic axis, said second part being pivotably attached to said first part for swivelling around a swivel axis relative to said first part so that said acoustic axis of said ultrasound transducer proceeds substantially through said focus and so that said swivel axis proceeds substantially through said focus, when said first part is attached at said therapeutic head.

2. A device as claimed in claim 1 wherein said second part comprises a bent part.

3. A device as claimed in claim 2 wherein said bent part comprises a substantially circularly curved part having a center of curvature which substantially coincides with said focus when said first part is attached at said therapeutic head.

4. A device as claimed in claim 2 wherein said bent part has a circumference, and further comprising means for adjusting said ultrasound transducer along said circumference.

5. A device as claimed in claim 2 wherein said bent part has a circumference, and further comprising a holding device adapted to receive said ultrasound transducer and means for mounting said holding device on said bent part allowing adjustment of said holding device and said ultrasound transducer along said circumference.

6. A device as claimed in claim 5 wherein said holder has a region adapted to receive said ultrasound transducer and wherein said holder is circularly curved at least in said region and has a center of curvature substantially coinciding with said focus.

7. A device as claimed in claim 6 wherein said region of said holder is adapted to adjustably receive said ultrasound transducer in a direction substantially perpendicular to said circumference.

8. A device as claimed in claim 2 wherein said bent part has a circumference and has an opening therein extending along a direction of said circumference, and further comprising a holder adapted to receive said ultrasound transducer mounted to said bent part for adjustment within said opening in said circumferential direction.

9. A device as claimed in claim 8 wherein said holder has a region adapted to receive said ultrasound transducer and wherein said holder is circularly curved at least in said region and has a center of curvature substantially coinciding with said focus.

10. A device as claimed in claim 9 wherein said region of said holder is adapted to adjustably receive said ultrasound transducer in a direction substantially perpendicular to said circumferential direction.

11. A device as claimed in claim 1 wherein said second part comprises a first bent element and a second bent element which are bent substantially parallel to each other and which are spaced from each other, and further comprising a holder adapted to receive said ultrasound transducer connected between said first and second bent elements.

12. A device as claimed in claim 1 wherein said swivel axis is a first swivel axis, and further comprising a third part pivotably connected to said second part for swivelling around a second swivel axis, said third part being adapted to hold said ultrasound transducer.

13. A device as claimed in claim 12 wherein said second swivel axis proceeds substantially through said focus.

14. A device as claimed in claim 1 wherein said second part comprises a plurality of elements which are movable relative to each other and which form a chain having a first element and a last element, and wherein said first element is pivotably attached to said first part for swivelling around said swivel axis and wherein said last element is adapted to receive said ultrasound transducer.

15. A device as claimed in claim 1 wherein said second part comprises a plurality of telescoping elements including a first telescoping element telescopically engaging said first part and a last telescoping element adapted to receive said ultrasound transducer.

16. A device as claimed in claim 1 wherein said second part comprises two spherically curved plates each having a center of curvature substantially coinciding with said focus when said device is attached at said therapeutic head, said two spherically curved plates being spaced from each other with a substantially constant gap therebetween and engaging said first part in said gap for swivelling around said swivel axis, and holding a curved part between said gap which is adapted to receive said ultrasound transducer.

17. A therapeutic apparatus comprising:
    a therapy head which emits acoustic waves converging at a focus, said therapy head having a plurality of attachment sites thereon; and a holding assembly having a first part attached to a selected one of said attachment sites and a second part adapted to receive an ultrasound transducer having an acoustic axis, said second part being pivotally attached to said first part for swivelling relative to said first part around a swivel axis so that said acoustic axis proceeds substantially through said focus and said swivel axis proceeding substantially through said focus.

18. A therapeutic apparatus as claimed in claim 17 wherein said second part comprises a bent part.

19. A therapeutic apparatus claim 18 wherein said bent part comprises a substantially circularly curved part having a center of curvature which substantially coincides with said focus when said first part is attached at said therapeutic head.

20. A therapeutic apparatus as claimed in claim 18 wherein said bent part has a circumference, and further comprising means for adjusting said ultrasound transducer along said circumference.

21. A therapeutic apparatus as claimed in claim 18 wherein said bent part has a circumference, and further comprising a holder adapted to receive said ultrasound transducer and means for mounting said holding device on said bent part allowing adjustment of said holding device and said ultrasound transducer along said circumference.

22. A therapeutic apparatus as claimed in claim 21 wherein said holder has a region adapted to receive said ultrasound transducer and wherein said holder is circularly curved at least in said region and has a center of curvature substantially coinciding with said focus.

23. A therapeutic apparatus as claimed in claim 22 wherein said region of said holder is adapted to adjustably receive said ultrasound transducer in a direction substantially perpendicular to said circumference.

24. A therapeutic apparatus as claimed in claim 18 wherein said bent part has a circumference and has an opening therein extending along a direction of said circumference, and further comprising a holder adapted to receive said ultrasound transducer mounted to said bent part for adjustment within said opening in said circumferential direction.

25. A therapeutic apparatus as claimed in claim 24 wherein said holder has a region adapted to receive said ultrasound transducer and wherein said holder is circularly curved at least in said region and has a center of curvature substantially coinciding with said focus.

26. A therapeutic apparatus as claimed in claim 25 wherein said region of said holder is adapted to adjustably receive said ultrasound transducer in a direction substantially perpendicular to said circumferential direction.

27. A therapeutic apparatus as claimed in claim 17 wherein said second part comprises a first bent element and a second bent element which are bent substantially parallel to each other and which are spaced from each other, and further comprising a holder adapted to receive said ultrasound transducer connected between said first and second bent elements.

28. A therapeutic apparatus as claimed in claim 17 wherein said swivel axis is a first swivelling axis, and further comprising a third part pivotably connected to said second part for swivelling around a second swivel axis, said third part being adapted to hold said ultrasound transducer.

29. A therapeutic apparatus as claimed in claim 28 wherein said second swivel axis proceeds substantially through said focus.

30. A therapeutic apparatus as claimed in claim 17 wherein said second part comprises a plurality of elements which are movable relative to each other and which form a chain having a first element and a last element, and wherein said first element is pivotably attached to said first part for swivelling around said swivel axis and wherein said last element is adapted to receive said ultrasound transducer.

31. A therapeutic apparatus as claimed in claim 17 wherein said second part comprises a plurality of telescoping elements including a first telescoping element telescopically engaging said first part and a last telescoping element adapted to receive said ultrasound transducer.

32. A therapeutic apparatus as claimed in claim 17 wherein said second part comprises two spherically curved plates each having a center of curvature substantially coinciding with said focus when said device is attached at said therapeutic head, said two spherically curved plates being spaced from each other with a substantially constant gap therebetween and engaging said first part in said gap for swivelling around said swivel axis, and holding a curved part between said gap which is adapted to receive said ultrasound transducer.

* * * * *